United States Patent
Jones et al.

(10) Patent No.: US 6,737,556 B2
(45) Date of Patent: May 18, 2004

(54) METHOD AND SYSTEM FOR REDUCING DECOMPOSITION BYPRODUCTS IN A METHANOL TO OLEFIN REACTOR SYSTEM

(75) Inventors: Jeffrey P. Jones, Houston, TX (US); Kenneth Ray Clem, Humble, TX (US); Stephen N. Vaughn, Kingwood, TX (US); Teng Xu, Houston, TX (US); Jeffrey L. White, Cary, NC (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/274,739

(22) Filed: Oct. 21, 2002

(65) Prior Publication Data

US 2004/0077912 A1 Apr. 22, 2004

(51) Int. Cl.⁷ .............................................. C07C 1/207
(52) U.S. Cl. ...................... 585/638; 585/639; 585/640; 585/920; 585/923
(58) Field of Search ................ 585/638, 640, 585/639, 920, 923

(56) References Cited

U.S. PATENT DOCUMENTS

| | | | |
|---|---|---|---|
| 3,847,793 A | 11/1974 | Schwartz et al. | 208/70 |
| 3,969,426 A | 7/1976 | Owen et al. | 260/668 R |
| 4,035,430 A | 7/1977 | Dwyer et al. | 260/668 R |
| 4,053,534 A | 10/1977 | Mitchell et al. | 260/683.15 R |
| 4,058,576 A | 11/1977 | Chang et al. | 260/673 |
| 4,399,305 A * | 8/1983 | Schreck | 562/607 |
| 4,542,252 A | 9/1985 | Graziani et al. | 585/640 |
| 4,814,517 A | 3/1989 | Trubac | 568/697 |
| 4,849,575 A | 7/1989 | Lewis | 585/640 |
| 5,573,990 A | 11/1996 | Wang et al. | 502/77 |
| 5,972,429 A | 10/1999 | Bayer et al. | 427/253 |
| 6,049,017 A | 4/2000 | Vora et al. | 585/324 |
| 6,121,504 A | 9/2000 | Kuechler et al. | 585/640 |
| 6,139,649 A | 10/2000 | Wynns | 148/277 |
| 6,165,286 A | 12/2000 | Bayer et al. | 148/220 |
| 6,166,282 A | 12/2000 | Miller | 585/638 |
| 6,403,854 B1 | 6/2002 | Miller et al. | 585/638 |

FOREIGN PATENT DOCUMENTS

JP 1090136 4/1989

OTHER PUBLICATIONS

"Alon Surface Technologies," [online], [retrieved on Jul. 3, 2002]. Retrieved from the Internet, http://www.alon.com/>, p. 1 of 1.

"Stainless Steel Composition" Chevron, [online ], [retrieved on Jul. 3, 2002]; can be accessed at: <http://www.sapiens.itgo.com/conversion_tables/stainless_steel_composition.htm>.

(List continued on next page.)

Primary Examiner—Thuan D. Dang

(57) ABSTRACT

Disclosed is a method and system for reducing the formation of metal catalyzed side-reaction byproducts formed in the feed vaporization and introduction system of a methanol to olefin reactor system by forming and/or coating one or more of the heating devices, feed lines or feed introduction nozzles of/with a material that is resistant to the formation of metal catalyzed side reaction byproducts. The invention also may include monitoring and/or maintaining the temperature of at least a portion of the feed vaporization and introduction system and/or of the feedstock contained therein below about 400° C., 350° C., 300° C., 250° C., 200° C. or below about 150° C. The temperature can be maintained in the desired range by jacketing at least a portion of the feed vaporization and introduction system, such as at least a portion of the feed introduction nozzle, with a thermally insulating material or by implementing a cooling system.

58 Claims, 3 Drawing Sheets

OTHER PUBLICATIONS

Baker et al., "Nickel–Base Material Solutions to Metal Dusting Problems," *Corrosion*, Paper No. 02394, pp. 1–16, (2002).

Helmenstine, "Why is Stainless Steel Stainless?,". [online], Chemistry, [retrieved in Jul. 3, 2002] Retrieved from the Internet, <http://chemistry.about.com/library/weekly/aa071201a.htm,>, pp. 1–2.

Perry et al., *Chemical Engineer's Handbook*, $5^{th}$ Edition, McGraw–Hill Book Co., New York pp. 3–219, 11–48, 20–65, 20–66, and 23–773 to 23–74 (1973).

The Hendrix Group, "Chemical Compositions Of Stainless Steels," [online], [retrieved on Jul. 3, 2003]. Retrieved from the Internet, <http://www.hghouston.com/ss_comp.html>, pp. 1–2.

* cited by examiner

US 6,737,556 B2

METHOD AND SYSTEM FOR REDUCING DECOMPOSITION BYPRODUCTS IN A METHANOL TO OLEFIN REACTOR SYSTEM

FIELD OF THE INVENTION

This invention is to a system and method for reducing methanol decomposition byproducts in a methanol to olefin reactor system. More particularly, the invention concerns reducing the formation of metal catalyzed side reaction byproducts by forming and/or coating at least a portion of the feed vaporization and introduction system, e.g., the feed introduction nozzle, with a material that reduces the formation of metal-catalyzed side reaction byproducts.

BACKGROUND OF THE INVENTION

Light olefins, defined herein as ethylene and propylene, serve as feeds for the production of numerous important chemicals and polymers. Light olefins traditionally are produced by cracking petroleum feeds. Because of the limited supply and escalating cost of petroleum feeds, the cost of producing olefins from petroleum sources has increased steadily. Efforts to develop and improve olefin production technologies, particularly light olefins production technologies, have increased.

In an oxygenate to olefin (OTO) reaction system, a feedstock containing an oxygenate is vaporized and introduced into a reactor. Exemplary oxygenates include alcohols such as methanol and ethanol, dimethyl ether, methyl ethyl ether, methyl formate, and dimethyl carbonate. In a methanol to olefin (MTO) reaction system, the oxygenate-containing feedstock includes methanol. In the reactor, the methanol contacts a catalyst under conditions effective to create desirable light olefins. Typically, molecular sieve catalysts have been used to convert oxygenate compounds to olefins. Silicoaluminophosphate (SAPO) molecular sieve catalysts are particularly desirable in such conversion processes because they are highly selective in the formation of ethylene and propylene.

In a typical MTO reactor system, undesirable byproducts may be fanned through side reactions. For example, the metals in conventional reactor walls may act as catalysts in one or more side reactions. If the methanol contacts the metal reactor wall at sufficient temperature and pressure, the methanol may be converted to undesirable methane and/or other byproducts. Byproduct formation in an MTO reactor is undesirable for several reasons. First, increased investment is required to separate and recover the byproducts from the desired light olefins. Additionally, as more byproducts are formed, less light olefins are synthesized. In other words, the production of byproducts is undesirable because methanol feed is consumed to produce the byproducts. Further, although the relative concentrations of metal catalyzed side reaction byproducts are generally quite low, the total amount of byproducts produced on an industrial scale can be enormous. Thus, it is desirable to decrease or eliminate the synthesis of byproducts in an MTO reactor system.

Sulfur-containing chemicals have proven effective for deactivating or passivating the metal surface of a reactor thereby reducing the formation of undesirable byproducts in the reactor. For example, Japanese Laid Open Patent Application JP 01090136 to Yoshinari et al. is directed to a method for preventing decomposition of methanol or dimethyl ether and coking by sulfiding the metal surface of a reactor. More particularly, the method includes reacting methanol and/or dimethyl ether in the presence of a catalyst at above 450° C. in a tubular reactor made of Iron and/or Nickel or stainless steel. The inside wall of the reactor is sulfided with a compound such as carbon disulfide, hydrogen disulfide or dimethyl sulfide. Additionally, a sulphur compound may be added to the feed.

Although passivating chemicals have proven effective in reducing metal catalyzed side reactions, the introduction of deactivating or passivating chemicals are problematic because these chemicals or their reaction products must be separated from the desired product. Thus, a need exists for a method and system for reducing the formation of metal catalyzed side reaction byproducts in an MTO reactor system while minimizing or eliminating the use of deactivating or passivating chemicals.

SUMMARY OF THE INVENTION

The present invention provides the ability to produce light olefins while reducing or eliminating the formation of metal catalyzed side reaction byproducts in a feed vaporization and introduction ("FVI") system. An FVI system is the region of the reactor system beginning at the point that at least a portion of the feedstock is in a vaporized state and extending to the point that the feedstock exits the feed introduction nozzle and enters the MTO reactor. As the resulting light olefin stream contains less metal catalyzed side reaction byproducts than is produced in conventional MTO reactor systems, olefin separation and purification costs can be reduced. The resulting purified olefin stream is particularly suitable for use as a feed in the manufacture of polyolefins.

One embodiment of the present invention provides a method for forming light-olefins from an oxygenate-containing feedstock, including directing the feedstock through a feed introduction nozzle attached to an MTO reactor and having an inner surface, at least a portion of which is fanned of a first material resistant to the formation of metal catalyzed side reaction byproducts. As defined herein, a material that is "resistant to the formation of metal catalyzed side reaction byproducts" is less catalytically active to the formation of metal catalyzed side reaction byproducts than carbon steel. After entering the reactor volume, methanol in the feedstock contacts a catalyst under conditions effective to form an effluent comprising light olefins.

The present invention also provides a feed vaporization and introduction system for an MTO reactor, comprising a teed introduction nozzle including a first generally tubular member having a first end for receiving a feedstock from a heating unit, a second end adjacent a reactor unit, and an inner surface forming a conduit for delivering the feedstock from the first end to the second end. At least a portion of the inner surface is formed of a first material that is resistant to the formation of metal catalyzed side reaction byproducts.

Optionally, the temperature of the feedstock and/or at least a portion of the FVI system is controlled with a thermally insulating material or a cooling system to further reduce the amount of metal catalyzed side reaction byproducts that is produced.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

Figure 1:
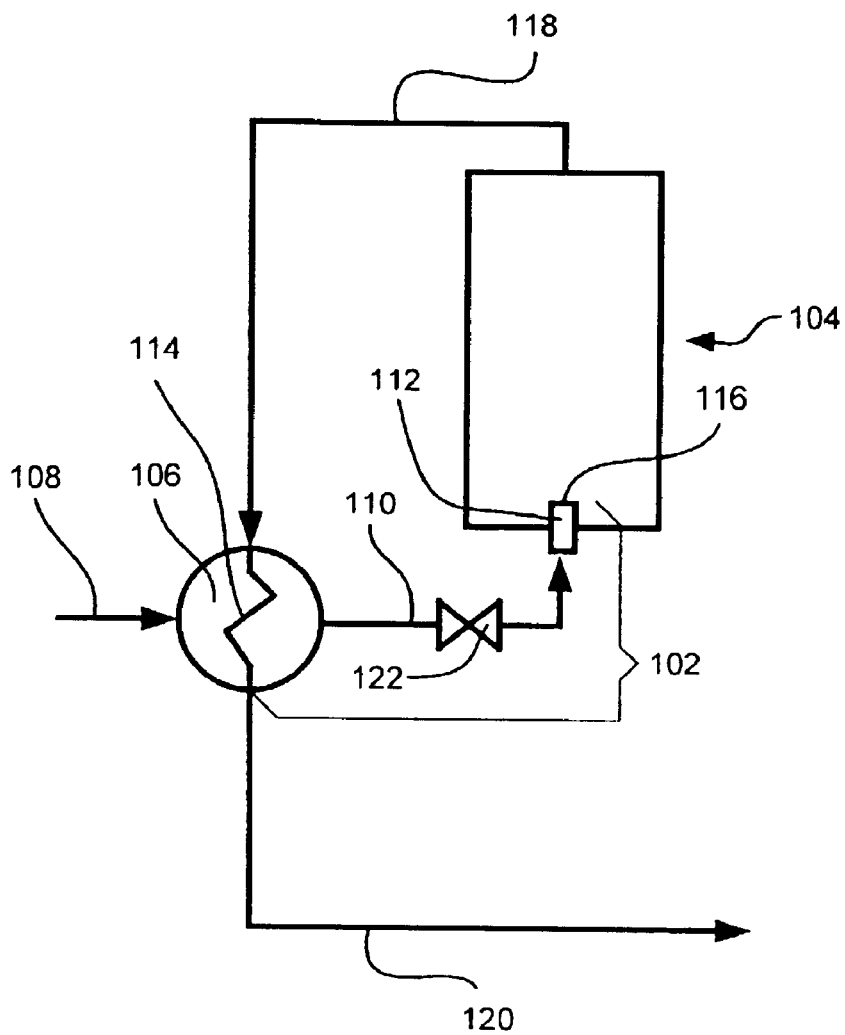
FIG. 1 illustrates a flow diagram of a methanol to olefin reactor system including the FVI system and the MTO reactor.

The present invention is directed to reducing or eliminating the formation of metal catalyzed side reaction byproducts in reactor systems, and in particular, in methanol to olefin (MTO) reactor systems. When a feedstock including an oxygenate such as methanol contacts a metal surface, e.g., the reactor walls, at relatively high temperatures and pressures, the oxygenate decomposes to form the undesirable byproducts. Iron and precious metals, such as Platinum and Palladium, are extremely active for methanol decomposition at high temperatures. The inventors have discovered that in addition to metal catalyzed side reactions occurring on reactor walls, metal catalyzed side reactions may occur before the feedstock enters the reactor. Before entering the reactor, the feedstock passes through a feed vaporization and introduction ("FVI") system wherein the feedstock is at least partially vaporized by one or more heating devices, is passed through feed lines to a feed introduction nozzle or nozzles, and is introduced into the reactor. The inner surface of at least a portion of the FVI system may be formed of metal which absorbs heat from the reactor volume thereby creating conditions in the FVI system that are conducive to the formation of metal catalyzed side reaction byproducts.

The present invention provides a method for making an olefin product from an oxygenate-containing feedstock while reducing the amount of reaction byproducts formed in the FVI system. In one embodiment, the method includes forming at least a portion of the FVI system, e.g., at least a portion of the feed introduction nozzle, particularly the inner surface of at least a portion of the FVI system, of one or more materials which is resistant to the formation of metal catalyzed side reaction byproducts. As defined herein, a material that is "resistant to the formation of metal catalyzed side reaction byproducts" is less catalytic to the formation of metal catalyzed side reaction byproducts than carbon steel. In another embodiment, the inner surface of the nozzle is coated with the material. Optionally, the entire feed introduction nozzle is be formed of a material resistant to the formation of metal catalyzed side reaction byproducts. In each of the above-described embodiments, the material is a metal alloy, an elemental metal, a non-metal, or a combination of the three. By reducing the formation of metal catalyzed side reaction byproducts, the time and costs associated with separating these byproducts from the desired product can be reduced or eliminated resulting in a significant commercial savings.

The method and system also includes, in one embodiment, maintaining at least a portion of the FVI system, e.g., the inner surface of at least a portion of the feed introduction nozzle, and/or the feedstock contained therein at a temperature effective to reduce or eliminate the formation of metal catalyzed side reaction byproducts in the FVI system. Preferably, the temperature of at least a portion of the inner walls of the FVI system will be less than the temper attire of the MTO reactor. In one embodiment of the present invention, the temperature of the inner walls of at least a portion of the FVI system, and/or the feedstock contained therein, is maintained below about 400° C., 350° C., 300° C., 250° C., 200° C., or below about 150° C.

Alternatively, as at least a portion of the FVI system, particularly the inner surface of at least a portion of the FVI system, is formed of one or more materials which is resistant to the formation of metal catalyzed side reaction byproducts, elevated temperatures in the FVI system can be tolerated in accordance with the present invention. Thus, the present invention is also directed to a method and system including maintaining at least a portion of the FVI system, e.g., the inner surface of at least a portion of the feed introduction nozzle, and/or the feedstock contained therein at an elevated temperature. The elevated temperature can be effective to superheat the feedstock. In one embodiment of the present invention, the temperature of the inner walls of at least a portion of the FVI system, and/or the feedstock contained therein, is maintained above 400° C., 450° C., 500° C., 550° C., 600° C., or above 650° C.

The inventors have discovered that as the feedstock passes through the FVI system, the oxygenate contacts the inner metal surface of one or more of the heating devices, the feed introduction nozzle or nozzles, and/or the lines connecting the heat exchangers to the feed introduction nozzles. In one side reaction in the FVI system, the metal surface of the heat exchangers, the lines and/or the feed introduction nozzles acts as a catalyst at high temperatures and converts some of the methanol in the feedstock to hydrogen, carbon monoxide, carbon dioxide, methane and/or graphite. This side reaction may be illustrated as follows:

Metal, Heat

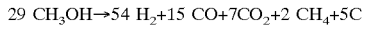

$$29\ CH_3OH \rightarrow 54\ H_2 + 15\ CO + 7CO_2 + 2\ CH_4 + 5C$$

The tendency of the FVI system to form undesirable metal catalyzed side-reaction byproducts is especially favorable because the ratio of metal surface area to quantity of feedstock is much higher in the FVI system than in the MTO reactor itself. The ratio of metal surface area to quantity of feedstock is particularly high in sparger nozzle and grid-type nozzle assemblies. In a grid type nozzle assembly, the feedstock is fed into an area beneath a grid which may be a flat or conical and which preferably includes a plurality of openings through which the feedstock passes as it enters the reactor volume. Additionally, in conventional MTO reactor systems, the temperature in the FVI system is conducive to the formation of metal catalyzed side-reaction byproducts because heat is transferred from hot material in the MTO reactor to the FVI system. The increased surface area of sparger and grid-type nozzle assemblies facilitates heat transfer from the reactor to the FVI system.

A portion of the feed introduction nozzle may extend into the reactor volume of the reactor further increasing the formation of metal catalyzed side reaction byproducts. The temperature within the reactor volume is generally much higher than the minimum temperatures that are conducive to the formation of metal catalyzed side reaction byproducts. Heat from the MTO reactor is transferred to the nozzle which may extend into the reactor volume. This heat transfer may be significantly increased if the nozzle protrudes into a dense phase zone of the reactor wherein heated solid particles continuously collide with the exterior surface of the nozzle. Accordingly, with conventional nozzle designs, the temperature of the metal-containing nozzle will increase to temperatures conducive to promote undesirable side reactions which are catalyzed by the heated inner metal surface of the nozzle. Thus, the formation of metal catalyzed side reaction byproducts is particularly a problem in feed introduction nozzles.

Further, as the feedstock contacts the inner surface of the FVI system at high weight hourly space velocities and under extreme temperature conditions, a portion of the inner surface of the FVI system can sheer or break away from the FVI system. This wastage facilitates the decomposition of the methanol-containing feedstock to side reaction byproducts. This concept, often referred to as "metal dusting," can be described as a catastrophic form of carbonization. The phenomenon can produce rapid metal wastage, producing pits and grooves as the affected metal disintegrates into a mixture of powdery carbon and metal particles. Metal dusting corrosion has negatively impacted the efficiency and productivity of processes within numerous industries. In MTO reactor systems, metal dusting facilitates the formation of metal catalyzed side reaction byproducts because the ratio of metal surface area to volume of feedstock increases as metal dusting occurs. In accordance with the present invention, the occurrence of metal dusting can be reduced or eliminated by coating or forming at least a portion of the FVI system, particularly the inner surface of at least a portion of the FVI system, of a material that is resistant to the formation of metal catalyzed side reaction byproduct.

Referring now to the drawings, FIG. 1 illustrates an MTO reactor system in accordance with one embodiment of the present invention. The MTO reactor system includes a feedstock vaporization and introduction system, or FVI system, which is generally designated by numeral 102, and an MTO reactor, which is generally designated by numeral 104. As defined herein, the FVI system 102 is a region of the reactor system beginning at the point that at least a portion of the feedstock is in a vaporized state and extending to the point that the feedstock exits the feed introduction nozzle and enters the MTO reactor, as illustrated in FIG. 1 At least a portion of the FVI system may be formed of one or more metals, or an alloy of metals to accommodate the temperature and pressure of the feedstock as it is transported to the reactor.

FIG. 1, a liquid oxygenate feedstock or feed stream 108 containing an oxygenate such as methanol is shown being directed to heating device 106 which heats the feedstock to a temperature just below, at or above the feedstock bubble point. Optionally, a series of heating devices may be implemented in the present invention to gradually heat the feedstock in steps as described in U.S. Pat. No. 6,121,504 to Kuechler et al., the entirety of which is incorporated herein by reference. If a series of heating devices is implemented in the present invention, a series of lines will transfer the feedstock between the heating devices to the feed introduction nozzle. The lines may be formed of a metal or alloy such as steel to accommodate the temperature and pressure of the feedstock. These metal lines or pipes in addition to the lines or pipes in the individual heating units may catalyze the formation of metal catalyzed side reaction byproducts. As a result, separation costs are increased and reaction efficiency is decreased.

One of ordinary skill in the art would recognize the various heating devices known in the art. Preferably, the heating device is a shell and tube heat exchanger wherein the heating medium may be product effluent 118, as shown in FIG. 1, a heat integration stream, e.g., from a water stripper or quench tower, or any other material having a higher temperature than the feedstock. Preferably, the heating device 106 will cause at least a portion of the feedstock stream to vaporize. The point at which at least a portion of the feedstock vaporizes is defined herein as the FVI system inlet 114. The FVI inlet may be within the heating device 106, the feed introduction nozzle 112 or anywhere therebetween.

After being heated in the heating device 106, the heated feedstock is directed through line or lines 110 to a feed introduction nozzle 112. Conventional feed introduction nozzles are formed of a metal or alloy such as carbon steel. The metal or alloy may act as a catalyst inside reactions at high temperatures to form undesirable byproducts. In accordance with the present invention, the nozzle may be formed, at least in part, of a material which is resistant to the formation of metal catalyzed side reaction byproducts. In another embodiment, the nozzle may be formed, at least in part, of a material that does not significantly promote the formation of metal catalyzed side reaction byproducts.

Figure 2:
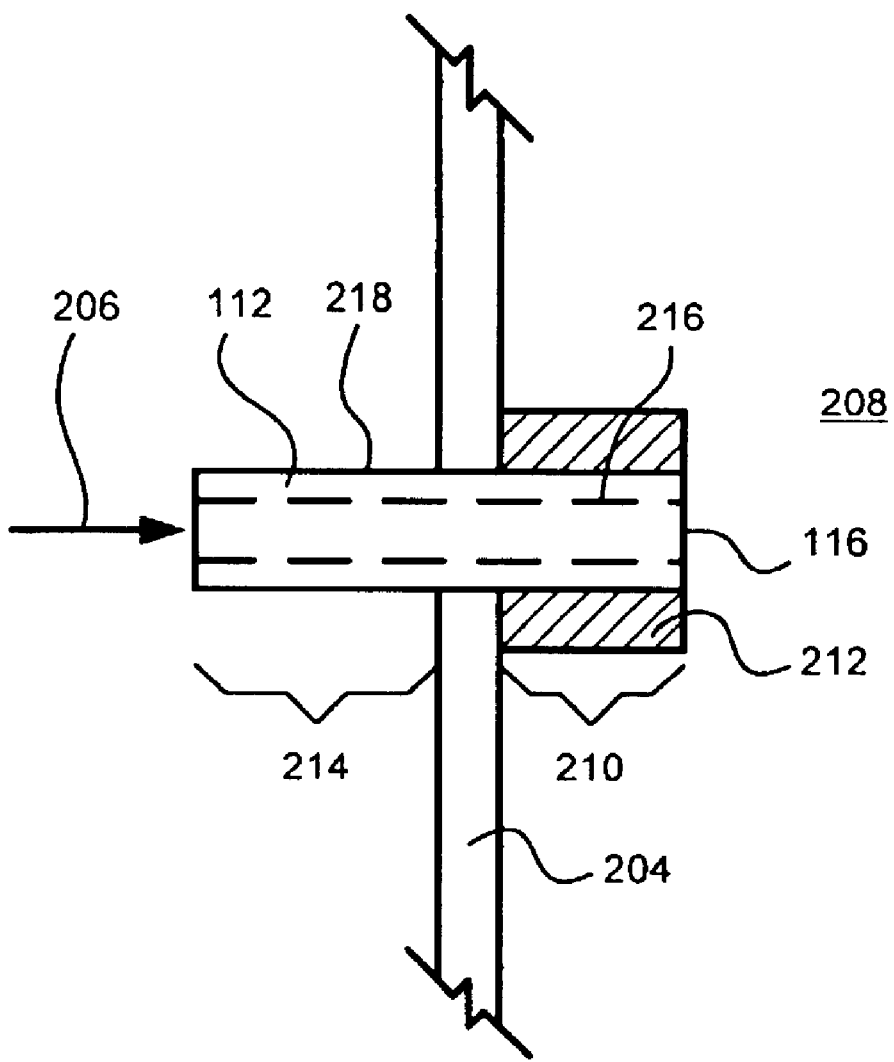
FIG. 2 illustrates a nozzle jacketing configuration in accordance with one embodiment of the present invention.
Figure 3:
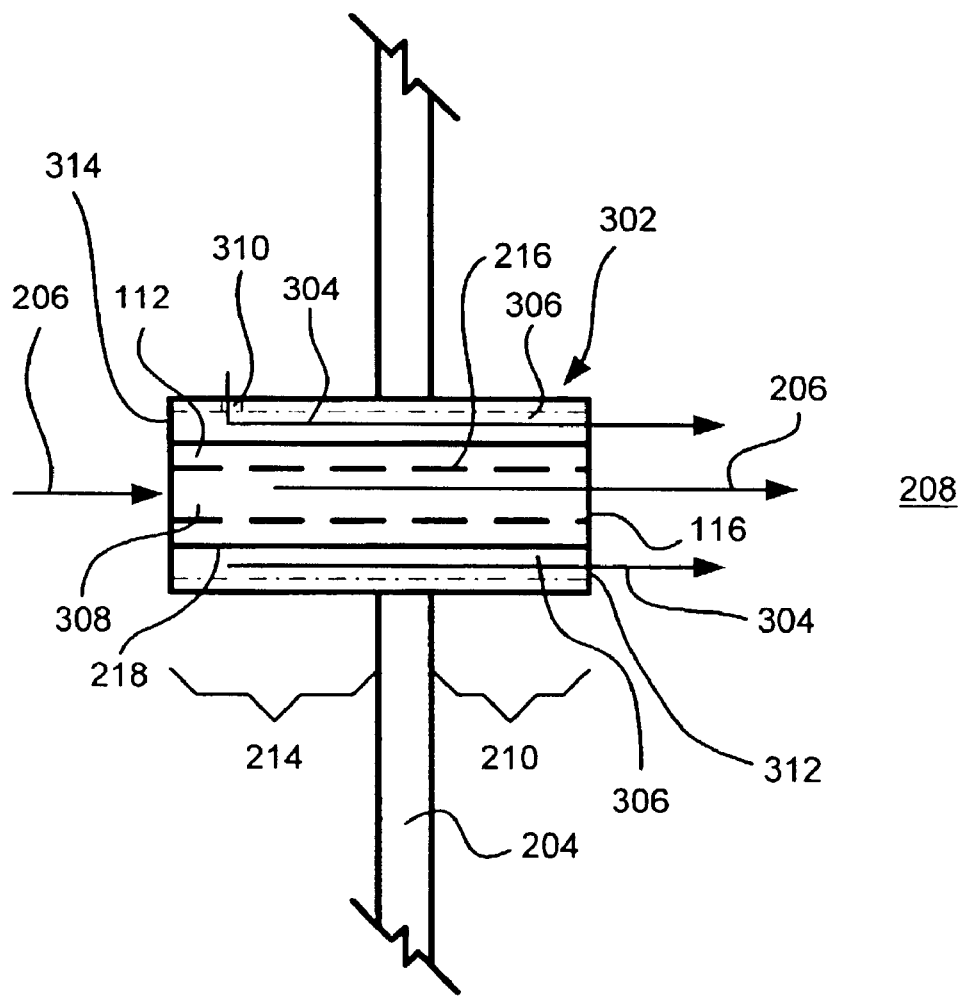
FIG. 3 illustrates a nozzle jacketing and cooling system in accordance with another embodiment of the present invention.

The nozzle may protrude into the MTO reactor volume, as illustrated in FIGS. 1–3. Alternatively, the portion of the nozzle adjacent the reactor may be oriented flush with the interior surface of the reactor wall. The heated feedstock passes through the feed introduction nozzle 112 and enters the MTO reactor 104.

The pressure in the MTO reactor may be less than the pressure of the feedstock within the FVI system, and the temperature within the MTO reactor may be much higher than the temperature in the FVI system. Accordingly, a portion or the entirety of the heated feedstock may vaporize as it exits the feed introduction nozzle and enters the MTO reactor. The point that the feedstock exits the feed introduction nozzle 112 and enters the MTO reactor 104 is defined herein as the FVI system outlet 116.

In the MTO reactor 104, the methanol in the feed stream contacts a molecular sieve catalyst under conditions effective to form an olefin product which exits the reactor in product effluent 118. As indicated above, the product effluent 118 from the MTO reactor 104 may be directed to the heat exchanger 106 in order to heat the feed stream 108. As shown in FIG. 1, after the product effluent 118 has heated the feed stream 108, it may be directed in line 120 to a product separation and purification system (not shown). Alternatively, the product effluent is directed to the product separation and purification system without first being directed to a heat exchanger.

In one embodiment of the present invention, at least a portion of the one or more heating devices, feed lines and/or feed introduction nozzles is formed, at least in part, of a material which does not substantially promote, e.g., is resistant to, the formation of metal catalyzed side reaction byproducts, as described above. The material can be an elemental metal, an alloy, or a nonmetal.

The composition of the material that is resistant to the formation of metal catalyzed side reaction byproducts, and that may be implemented in any portion of the FVI system, will now be described in greater detail. In one embodiment, at least a portion of the FVI system is formed of an alloy containing at least 10 weight percent nickel, preferably at least 30 weight percent nickel, more preferably at least 50 weight percent nickel and most preferably at least 60 weight percent nickel. In contrast, conventional feed introduction nozzles, e.g., formed of carbon steel, typically contain less than 10 weight percent nickel. Nickel-containing alloys are desirable because nickel oxide forms at the inner surface of the at least a portion of the FVI system. The nickel oxide coating layer on the inner surface of at least a portion of the FVI system is particularly resistant to the formation of metal catalyzed side reaction byproducts from a methanol-containing feedstock. Exemplary non-limiting alloys that contain at least 10 weight percent nickel include 263, 276, 302, 304, 305, 308, 309, 310, 314, 316, 317, 321, 330, 347, 409, 600, 601, 602CA, 617, 625LCF, 671, 690, 693, 754, 758, 800, 803, 825, 864, 904, CF-3, CF-8M, CH-20, CK-20, DS, HH, and HK. Exemplary non-limiting alloys that contain at least 30 weight percent nickel include 263, 276, 330, 400, 409, 600, 601, 602CA, 617, 625LCF, 671, 690, 693, 754, 758, 800, 803, 825, 864, DS, and TD. Exemplary non-limiting alloys that contain at least 50 weight percent nickel include 263, 276, 400, 600, 601, 602CA, 617, 625LCF, 671, 690, 693, 754, 758, and TD. Exemplary non-limiting alloys that contain at least 60 weight percent nickel include 400, 600, 601, 602CA, 625LCF, 693, 754, 758, arid TD.

Additionally or alternatively, the alloy contains at least 20 weight percent chromium, preferably at least 25 weight percent chromium, more preferably at least 30 weight percent chromium and most preferably at least 40 weight percent chromium. In contrast, conventional feed introduction nozzles formed of carbon steel typically contain less than 20 weight percent chromium. Chromium-containing alloys are desirable because chromium oxide forms at the inner surface of the at least a portion of the FVI system. The chromium oxide coating layer on the inner surface of the at least a portion of the FVI system is particularly resistant to the formation of metal catalyzed side reaction byproducts from a methanol-containing feedstock. Exemplary non-limiting alloys that contain at least 20 weight percent chromium include 309, 310, 329, 442, 446, 904L, 754, TD, 758, 693, 602CA, 625LCF, 601, 690, 671, 617, 263, 825, 803, 800, 864, 956 and 2205. Exemplary non-limiting alloys that contain at least 25 weight percent chromium include 310, 329, 758, 693, 602CA, 690, 671, and 803. Exemplary non-limiting alloys that contain at least 30 weight percent chromium include 758 and 671. Exemplary non-limiting alloys that contain at least 40 weight percent chromium include 671.

Additionally or alternatively, the alloy contains at least 2 weight percent aluminum, preferably at least 4 weight percent aluminum. In contrast, conventional feed introduction nozzles formed of carbon steel contain less than 2 weight percent aluminum. In accordance with the present invention, elemental aluminum or similar metal, e.g., palladium, cap also be implemented in the at least a portion of the FVI system if the temperature and reactor conditions are maintained below a level that would melt or rupture the at least a portion of the FVI system. Aluminum is particularly effective in reducing the formation of metal catalyzed side reaction byproducts from a methanol-containing feedstock. Aluminum-containing alloys are desirable because aluminum oxide forms at the inner surface of the at least a portion of the FVI system. The aluminum oxide coating layer on the inner surface of the at least a portion of the FVI system is particularly resistant to the formation of metal catalyzed side reaction byproducts from a methanol-containing feedstock. Exemplary non-limiting alloys that contain at least 2 weight percent aluminum include 602CA, 693 and 956. Exemplary non-limiting alloys that contain at least 4 weight percent aluminum include 956.

Iron is one non-limiting example of a metal which is particularly undesirable because of its effectiveness in forming metal catalyzed side reaction byproducts at high temperatures. Thus, in accordance with another embodiment of the present invention, the alloy additionally or alternatively contains less than 70 weight percent iron, preferably less than 50 weight percent iron, more preferably less than 30 weight percent iron, more preferably less than 10 weight percent iron, and most preferably less than 5 weight percent iron. In contrast, conventional feed introduction nozzles formed of carbon steel contain more than 70 weight percent iron. Iron is a particularly undesirable material in the FVI system because iron catalyzes the formation of side reaction byproducts from a methanol-containing feedstock. Exemplary non-limiting alloys that contain less than 70 weight percent iron include 263, 276, 330, 400, 600, 601, 602CA, 617, 625LCF, 671, 690, 693, 754, 758, 800, 803, 825, 864, DS, and TD. Exemplary non-limiting alloys that contain less than 50 weight percent iron include 263, 276, 330, 400, 600, 601, 602CA, 617, 625LCF, 671, 690, 693, 754, 758, 800, 803, 825, 864, DS, and TD. Exemplary non-limiting alloys that contain less than 30 weight percent iron include 276, 400, 600, 601, 602CA, 617, 625LCF, 671, 690, 693, 754, 758, 825, and TD. Exemplary non-limiting alloys that contain less than 10 weight percent iron include 276, 400, 600, 602CA, 617, 625LCF, 671, 690, 693, 754, 758, 825, and TD. Exemplary non-limiting alloys that contain less than 5 weight percent iron include 400, 617, 625LCF, 671, 693, 754, 758, 825, and TD.

Additionally or alternatively, the alloy contains at least 2 weight percent copper, preferably at least 15 weight percent copper, and more preferably at least 35 weight percent copper. In contrast, conventional feed introduction nozzles formed of carbon steel contain undetectable amounts of copper. In accordance with the present invention, elemental copper can also be implemented in the at least a portion of the FVI system if the temperature and reactor conditions are maintained below a level that would melt or rupture the at least a portion of the FVI system. Copper is particularly effective in reducing the formation of metal catalyzed side reaction byproducts from a methanol-containing feedstock. Exemplary non-limiting alloys that contain at least 2 weight percent copper include 825 and 400. An exemplary non-limiting alloy that contains at least 35 weight percent copper includes 400.

In another embodiment of the present invention, at least a portion of the FVI system is formed of an alloy selected from the group consisting of 410, 304, 316, 400, 330, 800, 600, 825, 601, 625, 617, 956, 693 and 671. Alternatively, at least a portion of the FVI system is formed of an alloy selected from the group consisting of TD, 758, 625, 601 and 276. Alternatively, at least a portion of the FVI system is formed of an alloy selected from the group consisting of 693, 602, 690, 671, 617, 263 and 956. In another embodiment, at least a portion of the FVI system, preferably the feed introduction nozzle, is formed of a material other than carbon steel.

Preferably, the material is an alloy resistant to the formation of metal catalyzed side reaction byproducts. Additionally or alternatively, the alloy is resistant to carbonization and metal dusting. See, e.g., Paper No. 02394 entitled *Nickle-Base Material Solutions to Metal Dusting Problems* from the Corrosion 2002 Conference, which is incorporated herein by reference. Table 1, below, provides a composition comparison of various commercial alloys that may be implemented in accordance with the present invention. Commercial variations are known to occur within the industry for each alloy provided below, and the compositional weight percentages provided herein are non-limiting.

TABLE 1

Approximate Compositions of Commercial Alloys

| Alloy | Ni | Cr | Fe | Mn | Si | Al | Ti | C | Other |
|---|---|---|---|---|---|---|---|---|---|
| 754 | 78 | 20 | — | — | — | 0.3 | 0.5 | 0.05 | 0.5 $Y_2O_3$ |
| TD | 73 | 22 | — | — | 1.4 | — | — | 0.01 | 3.0 Mo |
| 600 | 72 | 15.5 | 8 | 0.3 | 0.3 | 0.3 | 0.3 | 0.08 | — |
| 758 | 67 | 30 | — | — | — | 0.4 | 0.5 | 0.05 | 0.5 $Y_2O_3$ |
| 400 | 64 | 0.1 | 1.6 | 0.7 | 0.1 | 0.02 | 0.4 | 0.15 | 32.2 Cu |
| 693 | 62 | 29 | 4 | — | — | 3.1 | — | — | Nb, Zr |
| 602CA | 62 | 25 | 9.5 | — | — | 2.2 | — | 0.18 | Y, Zr |
| 625LCF | 61 | 21.5 | 2.5 | — | 0.1 | 0.2 | 0.2 | 0.02 | 9 Mo, 3.6 Nb |
| 601 | 60.5 | 23 | 13 | 0.2 | 0.2 | 1.4 | 0.4 | 0.05 | — |
| 690 | 59 | 29 | 9 | 0.2 | 0.1 | 0.3 | 0.3 | 0.02 | — |
| 276 | 57 | 15.5 | 5.5 | — | — | 0.1 | 0.2 | — | 3.8 W |
| 671 | 53 | 46 | — | — | — | 0.3 | 0.3 | 0.03 | — |
| 617 | 55 | 22 | 1 | — | 0.1 | 1.2 | 0.4 | 0.08 | 12.5 Co, 9.7 Mo |
| 263 | 51 | 20 | — | 0.3 | 0.1 | 0.5 | 2.2 | 0.06 | 20 Co, 5.9 Mo |
| 825 | 42 | 21.5 | 28 | 0.4 | 0.1 | 0.1 | 1 | 0.02 | 3 Mo, 2 Cu |
| DS | 37 | 16 | 41 | 1.0 | 2.3 | — | — | 0.08 | — |
| 330 | 35 | 19 | 44 | 1.0 | 1.3 | — | — | 0.07 | — |
| 302 | 10 | 18 | 70 | 1.0 | 1.0 | — | — | — | — |
| 304 | 9.25 | 19 | 68 | 2.0 | 1.0 | — | — | 0.08 | — |
| 316 | 12 | 17 | 65.5 | 2.0 | 1.0 | — | — | 0.08 | 2.5 Mo |
| 410 | — | 12.5 | 85.4 | 1.0 | 1.0 | — | — | 0.15 | — |
| 803 | 34 | 27 | 36 | 1.0 | 0.8 | 0.4 | 0.4 | 0.08 | — |
| 864 | 34 | 21 | 39 | 0.4 | 0.8 | 0.3 | 0.6 | 0.03 | 4.2 Mo |
| 800/800HT | 32 | 21 | 45 | 0.9 | 0.1 | 0.4 | 0.4 | 0.07 | — |
| 956 | — | 20 | 75 | — | — | 4.5 | 0.5 | 0.05 | 0.5 $Y_2O_3$ |

As indicated above, the material that is resistant to the formation of metal catalyzed side reaction byproducts may be a non-metal. Insulating materials that are capable of withstanding relatively high pressures and temperatures, e.g., those temperatures and pressures typical in the FVI system of an MTO reactor, are particularly effective at reducing the formation of metal catalyzed side reaction byproducts. Exemplary non-metals that may form at least a part of the FVI system include insulating materials such as ceramics, fire brick, high temperature calcium silicate, alumina and silica-alumina ceramics, diatomaceous silica brick and cements and fillers. In this embodiment, the inner surface of at least a portion of the FVI system, e.g., the feed introduction nozzle, is formed of the insulating material. For additional insulating materials which may be incorporated in the present invention, see *Petroleum Processing Handbook*, W. F. Bland and R. L. Davidson eds., McGraw Hill Publishers, pages 4–137 to 4–147 (1967), the entirety of which is incorporated herein by reference. The specific characteristics of the insulation, e.g., density, material and thickness, implemented in accordance with the present invention may be selected based on the specific reaction conditions inside the reactor, the composition and physical properties of the feedstock, and the composition and physical properties of the heating devices, lines, and/or feed introduction nozzles.

Optionally, the feed introduction nozzle, or other portion of the FVI system, is formed of an outer metal-containing tube or conduit mechanically or adhesively associated with an inner tube or conduit formed from one or more non-metal materials. The inner tube may be an insert within the outer metal-containing tube. Optionally, the insert is held in place against the outer conduit by mechanical interactions or with an adhesive. For example, the feed introduction nozzle may be formed of an outer metal nozzle having an inner insert formed of the insulating material. The insert includes a conduit through which the feedstock may pass as it is directed to the reactor unit. As the feedstock flows through the two-piece feed introduction nozzle, the feedstock contacts the insulating material which does not catalyzed the formation of side reaction byproducts. A minor amount of feedstock may pass through the pores of the non-metal material and contact the inner surface of the metal portion of the feed introduction nozzle. Thus, the metal portion of the feed introduction nozzle optionally is formed of an elemental or alloy material that is resistant to the formation of metal catalyzed side reaction byproducts, as described above.

Optionally, the outer material is formed of a non-metal material that does not catalyze the formation of side reaction byproducts from methanol. In this embodiment, the feed introduction nozzle is formed of two different non-metal materials that are resistant to the formation of metal catalyzed side reaction byproducts. Preferably, the outer material is a non-porous non-metal material in order to prevent leakage of the feedstock to the external environment.

In another embodiment of the present invention, the inner surface of the one or more of the heating devices, feed lines and/or feed introduction nozzles is coated with a material that is resistant to the formation of metal catalyzed side reaction byproducts. As the feedstock will contact the coating material, the feed introduction nozzle need not be formed of a material resistant to the formation of metal catalyzed side reaction byproducts. Thus, in this embodiment, one or more of the heating devices, feed lines and/or feed introduction nozzles optionally are formed of a material that is resistant to the formation of metal catalyzed side reaction byproducts. This embodiment provides the added benefit of allowing the retrofitting of an existing FVI system to provide for decreased formation of metal catalyzed side reaction byproducts without entirely replacing the existing FVI system.

The above-described materials which may be implemented in the embodiment of the present invention wherein at least a portion of the FVI system is formed of a material that is resistant to the formation of metal catalyzed side reaction byproducts may also be used as the coating material. Copper and copper alloys are also particularly effective as coating materials. Many methods for coating metal surfaces are known in the art. See, e.g., U.S. Pat. No. 6,139,649 to Wynns, U.S. Pat. No. 5,972,429 to Bayer et al., and U.S. Pat. No. 6,165,286 to Bayer et al., which are incorporated herein by reference.

As indicated above, the present invention may include maintaining the temperature of at least a portion of the FVI system and/or feedstock contained therein at a temperature effective to reduce or eliminate the formation of metal catalyzed side reaction byproducts. However, maintaining the temperature of the FVI system and/or feedstock contained therein is not necessary for the present invention because the FVI system is formed at least in part of a material which does not significantly promote the formation of metal catalyzed side reaction byproducts. Accordingly, the amount of side reaction byproducts produced by the FVI system in accordance with the present invention may be low or undetectable even at high temperatures.

One method of keeping the inner wall of at least a portion of the FVI system and/or of the feedstock contained therein at a temperature effective to reduce or eliminate the formation of metal catalyzed side reaction byproducts is to thermally insulate at least a portion of the FVI system, e.g., a portion or all of the feed introduction nozzle, with an insulating material. Non-limiting examples of insulating materials include: ceramics, fire brick, high temperature calcium silicate, alumina and silica-alumina ceramics, diatomaceous silica brick and cements and fillers. For additional insulating materials which may be incorporated in the present invention, see *Petroleum Processing Handbook*, W. F. Bland and R. L. Davidson eds., McGraw Hill Publishers, pages 4–137 to 4–147 (1967), the entirety of which is incorporated herein by reference. The specific characteristics of the insulation, e.g., density, material and thickness, implemented in accordance with the present invention may be selected based on the specific reaction conditions inside the reactor, the composition and physical properties of the feedstock, and the composition and physical properties of the heating device, lines, and/or feed introduction nozzle.

In another embodiment of the present invention, the temperature of the feed introduction nozzle, and/or of the inner metal-containing nozzle surface thereof and/or the feedstock itself, may be controlled with a cooling system. Many types of cooling systems could be implemented in the present invention. For example, the cooling system may include a cooling tube helically wrapped around the feed introduction nozzle. As cooling medium flows through the tube and around the feed introduction nozzle, the metal in the feed introduction nozzle as well as the feedstock flowing therethrough can be maintained at a temperature effective to minimize or eliminate the formation of metal catalyzed side-reaction byproducts.

In one embodiment of the present invention, the feedstock is maintained at a temperature effective to reduce, minimize or eliminate the formation of metal catalyzed side reaction byproducts. In this embodiment, the feedstock may act as a cooling agent for cooling the inner metal surface of one or more of the following portions of the FVI system: at least a portion of the heating device, at least a portion of the line, and/or at least a portion of the feed introduction nozzle. The desired temperature of the feedstock throughout the FVI system is preferably below about 400° C., 350° C., 300° C., 250° C., 200° C. or below about 150° C. These relatively low temperatures may be maintained by controlling the heating characteristics and number of the feedstock heating devices, and/or by insulating and/or cooling one or more of the following portions of the FVI system: at least a portion of the heating devices, at least a portion of the lines, and/or at least a portion of the feed introduction nozzles, as discussed in more detail below. Surprisingly and unexpectedly, the inventors have found that the introduction of a low temperature feedstock into a hot MTO reactor does not substantially affect the formation of light olefins in the MTO reactor.

Additionally or alternatively, the inventive method and system includes maintaining at least a portion of the inner surfaces of the feed vaporization and introduction system, e.g., the inner surface of the feed introduction nozzle, at a temperature effective to reduce or eliminate the formation of metal catalyzed side reaction byproducts. In accordance with the present invention, the temperature of the metal-containing inner surfaces of the FVI system may be maintained at the desired temperature in a variety of ways. For example, one or more of the heating devices, the lines between the feed heating devices and the feed introduction nozzle or nozzles, and/or the feed introduction nozzle itself may be jacketed with a thermally insulating material.

Additionally or alternatively, one or more of the heating devices, the lines between the feed heating devices and the feed introduction nozzle, and/or the feed introduction nozzle itself may include a cooling device for controlling the temperature of all or a portion of the FVI system. The invention is also directed to an FVI system having a temperature monitoring and controlling feature, and to feed introduction nozzles incorporating a jacket formed of a thermally insulating material and/or incorporating a cooling system.

As a non-limiting example, FIG. 2 illustrates one embodiment of the present invention which reduces or eliminates metal catalyzed side reaction byproduct formation caused by heat transfer from the MTO reactor to the inner surface of the feed introduction nozzle. A feed introduction nozzle 112 is shown in FIG. 2 penetrating the reactor wall 204. The portion of the feed introduction nozzle which is inside the reactor volume 208 is identified as the internal nozzle section 210. Methanol stream 206 from the heating device (not shown) travels through a line or pipe (not shown) and enters the feed introduction nozzle 112. The methanol stream 206 passes through the feed introduction nozzle 112 and enters the inner reactor volume 208 wherein the methanol contacts a catalyst under conditions effective to convert the methanol to light olefins. An insulating material 212 covers at least a portion of the outer nozzle surface 218 of the internal nozzle section 210 of the feed introduction nozzle 112. The insulating material reduces the quantity of heat that is transferred from the reactor volume 208 to the internal nozzle section 210 of the feed introduction nozzle 112. As a result, the metal on the inner nozzle surface 216 of the feed introduction nozzle can be maintained at a temperature effective to reduce, minimize or eliminate the formation of metal-catalyzed side reaction byproducts.

Although a portion of the feed introduction nozzle 112 adjacent the FVI system outlet 116 may be exposed to the reactor volume 208, the amount of heat transferred from the reactor volume to the portion of the inner nozzle surface 216 of the feed introduction nozzle that is adjacent the FVI system outlet 116 is minimal because the feedstock may tend to cool the inner nozzle surface 216 adjacent the FVI system outlet. Beneficially, only a relatively small amount of hot material in the reactor will contact the FVI system outlet 116 because the flow characteristics of the feedstock as it enters the reactor volume 208 will tend to direct the hot material away from the FVI system outlet 116. Accordingly, even the portion of the inner nozzle surface 216 that is adjacent the FVI system outlet 116 can be maintained at temperatures effective to reduce, minimize or eliminate the formation of metal catalyzed side reaction byproducts. In other words, to the extent that heat is transferred from the hot material in the reactor to the portion of the feed introduction nozzle that is adjacent the FVI system outlet 116, the amount of metal catalyzed side reaction byproducts formed in that region is negligible.

FIG. 2 illustrates the insulating material 212 covering the entire internal nozzle section 210 of the feed introduction nozzle 112. Optionally, the insulating material 212 may cover a portion of the internal nozzle section 210 of the feed introduction nozzle 112. Additionally or alternatively, the insulating material may cover a portion of the FVI outlet 116. Similarly, the insulating material may additionally or alternatively provide increased thermal protection for the metal contained in the feed introduction nozzle and the feedstock contained in the FVI system by extending the insulating material into and/or through the reactor wall 204. In this embodiment, the opening in the reactor wall through which the feed introduction nozzle extends must be increased in size in order to allow the insulating material to traverse the reactor wall. Optionally, the insulating material 212 may also extend to cover all or a portion of the external nozzle section 214 of the feed introduction nozzle 112. The insulating material may extend to cover additional areas of the FVI system. For example, the insulating material may cover all or a portion of the heating devices and/or the lines directing the feedstock from the heating devices to the feed introduction nozzle.

In another non-limiting example, FIG. 3 illustrates an embodiment of the present invention wherein the feed introduction nozzle 112 includes a cooling system generally designated by numeral 302. As shown in FIG. 3, the feed introduction nozzle 112is a generally cylindrical tube defining a feedstock pathway 308. A second larger diameter cylindrical tube is oriented coaxially to the feed introduction nozzle 112 thereby forming an outer cooling pathway 306 around the feedstock pathway 308. A cooling medium 304, such as water or a cooling steam, e.g., from a water stripper or quench tower, or any other material having a lower temperature than the feedstock in the feed introduction nozzle, is introduced into cooling pathway 306 at cooling inlet 310 and is circulated in the cooling pathway 306 around the feedstock in the feedstock pathway 308. Preferably, exterior nozzle end 314 of the cooling pathway 306 is closed-off so that the cooling medium flows toward the reactor. As feedstock passes through the feedstock pathway 306 toward the MTO reactor, the cooling medium 304 is passed through the cooling pathway 306 and withdraws heat from the feed introduction nozzle and/or the feedstock. By cooling the feedstock and the inner nozzle surface 216 of the feed introduction nozzle, the feed introduction nozzle 112 and/or the feedstock can be maintained at a temperature effective to minimize or eliminate the formation of metal catalyzed side reaction byproducts.

This embodiment of the present invention has the additional advantage of providing the ability to control and vary the temperature of the feedstock and of the feed introduction nozzle. For example, the temperature of the feedstock/feed introduction nozzle can be modified by varying the flow rate and/or temperature of the cooling medium which passes over the nozzle and feedstock pathway.

The cooling medium 304 may exit the feed introduction nozzle within the reactor through diluent outlet 312, as shown in FIG. 3, or outside of the reactor through a cooling medium outlet (not shown). If the cooling medium 304 exits the feed introduction nozzle within the reactor through diluent outlet 312, the cooling medium will mix with the oxygenate feedstock inside the reactor. In this manner, the invention provides an additional advantage in that the partial pressure of the oxygenate introduced into the MTO reactor may be carefully controlled in order to obtain a desired product selectivity and/or oxygenate conversion as discussed, for example, in U.S. patent application Ser. No. 09/506,843 to Fung et al., the entirety of which is incorporated herein by reference. Thus, the cooling medium may be selected from one or more of the diluents more fully discussed below.

FIG. 3 illustrates the cooling system 302 traversing the reactor wall 204 and covering the entire surface of the feed introduction nozzle. Optionally, the cooling system 302 may provide thermal protection for a portion of the feed introduction nozzle rather than the entire feed introduction nozzle. For example, the cooling system 302 may cover the entirety or only a portion of the internal nozzle section 210 of the teed introduction nozzle 112. In this embodiment, the cooling system may, or may not, extend partially or entirely through the reactor wall 204. Similarly, the cooling system 302 may cover all or a portion of the external nozzle section 214. The cooling system may extend to cover additional areas of the FVI system. For example, the cooling system may cover all or a portion of the heating device(s) and/or the line(s) directing the feedstock from the heating device(s) to the feed introduction nozzle.

In accordance with the present invention, the jacketing and cooling embodiments, discussed above, may be combined. For example, the nozzle may include a feedstock pathway, a cooling system and a jacket formed of one or more of the thermally insulating materials discussed above. Either the jacket or the cooling system may be the outermost layer depending on the MTO reactor conditions, the cooling medium used, the physical properties of the nozzle, the physical properties of the heating devices and the physical properties of the lines connecting the heating devices to the feed introduction nozzle. Additionally or alternatively, a plurality of the same or different jacketing layers and/or the same or different cooling systems may be implemented in the present invention.

Additionally or alternatively, the jacketing and/or cooling embodiments may be combined with the low temperature feedstock embodiment. By coupling the low temperature feedstock throughout the FVI system, e.g., below about 400° C., 350° C., 300° C., 250° C., 200° C., or below about 150° C., with the insulating and/or cooling system embodiments, the temperature of the metal-containing inner surface of at least a portion of the FVI system can be maintained at a temperature effective to reduce or eliminate the formation of metal catalyzed side reaction byproducts, e.g., below about 400° C., 350° C., 300° C., 250° C., 200° C., or below about 150° C.

In one embodiment, the inner metal-containing surface(s) of the FVI system may be maintained at a temperature effective to maintain the feedstock at liquid-vapor equilibrium throughout the FVI system. Because the feedstock is maintained at a temperature effective to maintain the feedstock in a liquid-vapor equilibrium throughout the FVI system, superheating of the vapor is minimized or eliminated thereby reducing the formation of reaction byproducts through metal-catalyzed side reactions. Alternatively, the feedstock may be entirely vaporized prior to entering the reactor. For example, the feedstock may pass through a valve 122 in line 110, as shown in FIG. 1, wherein the feed is subjected to a pressure drop and the feedstock is further vaporized. The feedstock may be superheated so long as the temperature of the superheated feedstock is maintained below temperatures conducive to the formation of metal catalyzed side reaction byproducts.

The invention also provides for the ability to monitor the temperature of any point along the FVI system including one or more of the heating devices, the lines, and/or the feed introduction nozzle. For example, a thermocouple may be implemented on the inner and/or outer surface of the feed introduction nozzle and/or on the inner and/or outer surface of the cooling system or insulating material. By incorporating a thermocouple in the present invention, the temperature of the feedstock and/or of the metal in the feed introduction nozzle may be monitored to determine whether conditions are conducive to the formation of metal catalyzed side-reaction byproducts. Moreover, with the cooling system embodiment of the present invention, the characteristics of the cooling medium may be modified responsive to variations in temperature of any inner or outer nozzle surfaces. For example, as the monitored temperature of the inner surface of the nozzle approaches temperatures conducive to the formation of metal catalyzed side reaction byproducts, the characteristics of the cooling medium, e.g., flow rate and/or temperature, may be modified to lower the temperature of the inner nozzle surface to non-reactive temperatures.

Preferably, the conditions in the MTO reactor including the pressure, temperature, weight hourly space velocity (WHSV), etc., are conducive to converting the methanol to light olefins, as discussed in more detail below. In accordance with the present invention, at least a portion of the FVI system, especially the feed introduction nozzle, is monitored and/or maintained at conditions, e.g., temperatures, effective to reduce, minimize or substantially eliminate the formation of metal catalyzed side-reaction byproducts irrespective of the conditions within the MTO reactor. That is, the conditions within the MTO reactor may or may not be conducive to the formation of metal catalyzed side-reaction byproducts. Thus, the present invention may be implemented with a deactivated or passivated reactor.

Typically, molecular sieve catalysts have been used to convert oxygenate compounds to light olefins. Silicoaluminophosphate (SAPO) molecular sieve catalysts are particularly desirable in such a conversion process, because they are highly selective in the formation of ethylene and propylene.

The feedstock preferably contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In one preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbon atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbon atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as gas-to-oletins (GTO) or alternatively, methanol-to-olefins. In an MTO process, a methanol containing feedstock is converted in the presence of a molecular sieve catalyst composition into one or more olefins, preferably and predominantly, ethylene and/or propylene, often referred to as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference. Dual riser reactors or other reactor designs optionally include a plurality of feed introduction nozzles, which may be formed and/or coated with a material resistant to the formation of metal catalyzed side reaction byproducts in accordance with the present invention.

The preferred reactor types are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/156,4613 filed May 4, 2000 (multiple riser reactor), which are all herein fully incorporated by reference.

In one embodiment, the amount of liquid feedstock fed separately or jointly with a vapor feedstock to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment the WHSV is greater than 20 $hr^{-1}$, preferably the WHSV for conversion of a feedstock containing methanol, dimethyl ether, or both, is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. Pat. application Ser. No. 09/708,753 filed Nov. 8, 2000, which is herein incorporated by reference.

EXAMPLE

In order to provide a better understanding of the present invention including representative advantages thereof, the following example is offered. The example compares the reactivity of a methanol feedstock in a stainless steel reactor at various temperatures with the reactivity of a passivated reactor.

All data presented was obtained using a microflow reactor. The microflow reactor used was a No. 316 stainless steel reactor (¼ inch outer diameter) located in a furnace to which vaporized methanol was fed. 316 stainless steel is less catalytically active to the formation of metal catalyzed side reaction byproducts than carbon steel, and is thus resistant to the formation of metal catalyzed side reaction byproducts in accordance with the present invention.

The vaporized methanol was maintained at 120° C. The methanol conversion reactions were performed at 25 psig (172 kPag) methanol pressure and at a methanol 80 $\mu$l/min. The control experiment was performed under identical reaction conditions except that a coated reactor was used. The coated reactor was ¹⁄₁₆ inch in diameter and was made of steel coated with a thin layer of fused silica.

The effluent from the reactor was collected in a 15-sample loop Valco valve. The collected samples were analyzed by on-line gas chromatography (Hewlett Packard 6890) equipped with a flame ionization detector. CO, $CO_2$ and $H^2$ were not analyzed. The measured conversions of methanol, which were calculated on the carbon basis, would have been higher if CO, $CO_2$ and $H_2$ were included in the calculations. The chromatographic column used was a Q-column.

Table 2 summarizes the results of the conversions (Wt. %) of methanol reacting on the lab reactor.

TABLE 2

Methanol conversions (Wt. %) from Methanol Reacting on Stainless Steel Reactor Wall

| Temperature (° C.) | Methanol Conversion (Wt. %) | |
| --- | --- | --- |
| | 316 Stainless Steel Reactor | Coated Reactor |
| 200 | 0.02 | 0.00 |
| 300 | 0.04 | 0.00 |
| 350 | 0.15 | 0.00 |
| 400 | 0.34 | 0.01 |
| 450 | 0.91 | 0.04 |
| 500 | 3.46 | 0.06 |
| 550 | 5.79 | 0.16 |

According to the results indicated above, in accordance with the present invention, a negligible amount of metal catalyzed side reaction byproducts were detected below 350° C. in a No. 316 stainless steel reactor. At 350° C., 0.15 wt % methanol conversion was observed in an untreated stainless steel reactor. The conversion was much higher at 500° C. and 550° C. Methanol decomposition would be significantly greater for conventional carbon steel because of its high iron content. The conversion of methanol on the coated reactor was essentially zero even at 500° C. This experimental data indicates that No. 316 stainless steel in a reactor is resistant to the formation of metal catalyst side reaction byproducts below about 450° C., although No. 316 stainless steel is more active for decomposing methanol at higher temperatures. Moreover, this data indicates that undesirable reaction byproducts can be minimized by maintaining the methanol feedstock at a temperature lower than the MTO reactor temperature.

In another embodiment of the present invention, the percent conversion of oxygenate over the surface of a metal reactor, preferably in the absence of a MTO catalyst, is less than 1.0 percent, preferably less than 0.8 percent, more preferably less than 0.4 percent, and most preferably less than 0.05, e.g., below detection limits. In other words, the invention includes maintaining the feedstock while it is in the FVI system, especially the feed introduction nozzle, at conditions, e.g., temperature, effective to substantially eliminate the formation of metal catalyzed side reaction byproducts. "Substantially eliminate" is defined herein as less than 0.05 percent conversion to byproducts excluding CO, $CO_2$ and $H_2$.

Having now fully described the invention, it will be appreciated by those skilled in the art that the invention can be performed within a wide range of parameters within what is claimed, without departing from the spirit and scope of the invention.

What is claimed is:

1. A method for forming light-olefins from a feedstock comprising alcohols and/or ethers, the process, comprising:
   directing the feedstock through a feed introduction nozzle attached to a reactor and having an inner surface, at least a portion of which is formed of a first material that is resistant to the formation of metal catalyzed side reaction byproducts; and
   contacting, in the reactor, the feedstock with a molecular sieve catalyst under conditions effective to form an effluent comprising the light olefins.

2. The method of claim 1, wherein the nozzle is formed, at least in part, of the first material.

3. The method of claim 2, wherein the first material is an alloy selected from the group consisting of 410, 304, 316, 400, 330, 800, 600, 825, 601, 625, 617, 956, 693 and 671.

4. The method of claim 2, wherein the first material comprises at least 20 weight percent chromium.

5. The method of claim 4, wherein the first material comprises at least 25 weight percent chromium.

6. The method of claim 5, wherein the first material comprises at least 30 weight percent chromium.

7. The method of claim 6, wherein the first material comprises at least 40 weight percent chromium.

8. The method of claim 2, wherein the first material comprises at least 10 weight percent nickel.

9. The method of claim 8, wherein the first material comprises at least 30 weight percent nickel.

10. The method of claim 9, wherein the first material comprises at least 50 weight percent nickel.

11. The method of claim 10, wherein the first material comprises at least 60 weight percent nickel.

12. The method of claim 2, wherein the first material comprises at least 2 weight percent aluminum.

13. The method of claim 12, wherein the first material comprises at least 4 weight percent aluminum.

14. The method of claim 2, wherein the first material comprises less than 70 weight percent iron.

15. The method of claim 14, wherein the first material comprises less than 50 weight percent iron.

16. The method of claim 15, wherein the first material comprises less than 30 weight percent iron.

17. The method of claim 16, wherein the first material comprises less than 10 weight percent iron.

18. The method of claim 17, wherein the first material comprises less than 5 weight percent iron.

19. The method of claim 1, wherein the feed introduction nozzle comprises an inner coating layer forming the inner surface, the coating layer being formed, at least in part, of the first material.

20. The method of claim 19, wherein the first material comprises at least 20 weight percent chromium.

21. The method of claim 20, wherein the first material comprises at least 25 weight percent chromium.

22. The method of claim 21, wherein the first material comprises at least 30 weight percent chromium.

23. The method of claim 22, wherein the first material comprises at least 40 weight percent chromium.

24. The method of claim 19, wherein the first material comprises at least 10 weight percent nickel.

25. The method of claim 24, wherein the first material comprises at least 30 weight percent nickel.

26. The method of claim 25, wherein the first material comprises at least 50 weight percent nickel.

27. The method of claim 26, wherein the first material comprises at least 60 weight percent nickel.

28. The method of claim 19, wherein the first material comprises at least 2 weight percent aluminum.

29. The method of claim 28, wherein the first material comprises at least 4 weight percent aluminum.

30. The method of claim 19, wherein the first material comprises less than 70 weight percent iron.

31. The method of claim 30, wherein the fist material comprises less than 50 weight percent iron.

32. The method of claim 31, wherein the first material comprises less than 30 weight percent iron.

33. The method of claim 32, wherein the first material comprises less than 10 weight percent iron.

34. The method of claim 33, wherein the first material comprises less than 5 weight percent iron.

35. The method of claim 19, wherein e first material is any material other than carbon steel.

36. The method of claim 1, further comprising:
   maintaining the inner surface of the nozzle at a temperature below 400° C.

37. The method of claim 36, wherein the inner surface of the nozzle is maintained at a temperature below 300° C.

38. The method of claim 37, wherein the inner surface of the nozzle is maintained at a temperature below 200° C.

39. The method of claim 1, wherein the inner surface of the nozzle is maintained at a temperature above 500° C.

40. The method of claim 39, wherein the inner surface of the nozzle is maintained at a temperature above 650° C.

41. The method of claim 36, further comprising:
   cooling at least a portion of the inner surface of the nozzle with a cooling system.

42. The method of claim 36, wherein the nozzle is jacketed with a thermally insulating material.

43. The method of claim 42, wherein the insulating material is selected from the group consisting of fire brick, high temperature calcium silicate, alumina and silica-alumina ceramics, diatomaceous silica brick and cements, and fillers.

44. The method of claim 42, wherein the thermally insulating material covers at least a portion of an interior portion of the nozzle extending inside the reactor.

45. The method of claim 1, further comprising:
   maintaining the feedstock below 400° C. while the feedstock is in the nozzle.

46. The method of claim 45, wherein the feedstock is maintained below 350° C. while the feedstock is in the nozzle.

47. The method of claim 46, wherein the feedstock is maintained below 250° C. while the feedstock is in the nozzle.

48. The method of claim 47, wherein the feedstock is maintained below 200° C. while the feedstock is in the nozzle.

49. The method of claim 1, wherein the feedstock is superheated while the feedstock is in the nozzle.

50. The method of claim 1, further comprising:
maintaining the nozzle at conditions effective to produce less than 0.8 weight percent of metal catalyzed side reaction byproducts excluding CO, $CO_2$ and $H_2$.

51. The method of claim 50, wherein the conditions are effective to produce less than 0.4 weight percent of metal catalyzed side reaction byproducts excluding CO, $CO_2$ and $H_2$.

52. The method of claim 51, wherein the conditions are effective to substantially eliminate the formation of metal catalyzed side reaction byproducts.

53. The method of claim 1, wherein the first material is an alloy selected from the group consisting of TD, 758, 625, 601 and 276.

54. The method of claim 1, wherein the first material is an alloy selected from the group consisting of 693, 602, 690, 671, 617, 263 and 956.

55. The method of claim 2, wherein the first material comprises at least two weight percent copper.

56. The method of claim 55, wherein the first material comprises at least 15 weight percent copper.

57. The method of claim 56, wherein the first material comprises at least 35 weight percent copper.

58. The method of claim 2, wherein the first material is on alloy selected from the group consisting of 825 and 400.

* * * * *